United States Patent
Maruta et al.

(10) Patent No.: US 10,058,618 B2
(45) Date of Patent: Aug. 28, 2018

(54) PAK1-BLOCKING 1,2,3-TRIAZOLYL ESTERS

(71) Applicant: Hiroshi Maruta, Brunswick West, Victoria (AU)

(72) Inventors: Hiroshi Maruta, Victoria (JP); Hideaki Takahashi, Tokushima (JP); Yoshihiro Uto, Tokushima (JP); Binh Cao Quan Ngyuen, Okinawa (JP); Pham Thi Be Tu, Okinawa (JP); Shinkichi Tawata, Okinawa (JP)

( * ) Notice: Subject to any disclaimer, the term of this patent is extended or adjusted under 35 U.S.C. 154(b) by 0 days.

(21) Appl. No.: 15/364,416

(22) Filed: Nov. 30, 2016

(65) Prior Publication Data

US 2017/0224830 A1     Aug. 10, 2017

(30) Foreign Application Priority Data

Feb. 10, 2016 (AU) .................. 2016900442

(51) Int. Cl.

| | |
|---|---|
| *C07D 249/06* | (2006.01) |
| *C07D 487/04* | (2006.01) |
| *A61K 31/4192* | (2006.01) |
| *A61K 31/407* | (2006.01) |
| *A61K 31/192* | (2006.01) |
| *A61K 31/403* | (2006.01) |
| *A61K 47/48* | (2006.01) |

(52) U.S. Cl.
CPC ...... *A61K 47/48061* (2013.01); *A61K 31/192* (2013.01); *A61K 31/403* (2013.01); *A61K 31/407* (2013.01); *A61K 31/4192* (2013.01); *C07D 249/06* (2013.01); *C07D 487/04* (2013.01)

(58) Field of Classification Search
None
See application file for complete search history.

(56) References Cited

PUBLICATIONS

Nguyen, et al., Euro. J. Med. Chem., 126:270 (available online Nov. 20, 2016). (Year: 2017).*
Maruta, H. Herbal Therapeutics that Block the Oncogenic Kinase PAK1: A Practical Approach towards PAK1-dependent Diseases and Longevity. Phytother Res 28:656-72 (2014).
Hirokawa et al. Signal therapy of human pancreatic cancer and NF1-deficient breast cancer xenograft in mice by a combination of PP1 and GL-2003, anti-PAK1 drugs (Tyr-kinase inhibitors). Cancer Lett. 245:242-51 (2007).
Guo et al. R-ketorolac Targets Cdc42 and Rac1 and Alters Ovarian Cancer Cell Behaviors Critical for Invasion and Metastasis. Mol Cancer Ther. 14:2215-27 (2015).
Nguyen et al. Combination of immunoprecipitation (IP)-ATP_Glo kinase assay and melanogenesis for the assessment of potent and safe PAK1-blockers in cell culture. Drug Discov Ther. 9:289-295 (2015).
Nguyen et al. Mimosine Dipeptide Enantiomsers: Improved Inhibitors against Melanogenesis and Cyclooxygenase. Molecules, 20:14334-14347 (2015).

* cited by examiner

*Primary Examiner* — Michael Barker
(74) *Attorney, Agent, or Firm* — Benjamin Aaron Adler (57) ABSTRACT

The present invention relates to a PAK1 blocking compound having a much higher bioavailability and cell permeability than traditional herbal PAK1 blockers or synthetic PAK1 blockers, and the uses thereof for treating cancer or other PAK1 dependent diseases or disorders. This PAK1 blocking compound comprises an ester of an acidic PAK1 blocker, or a pharmaceutically acceptable salt thereof. This PAK1-blocking ester may be prepared by esterifying a PAK1 blocker starting material with an alcohol; and treating the esterified PAK1 blocker with an aromatic azide to generate a 1,2,3-triazolyl derivative.

15 Claims, 3 Drawing Sheets

PAK1-BLOCKING 1,2,3-TRIAZOLYL ESTERS

CROSS-REFERENCE TO RELATED APPLICATIONS

This application claims benefit of priority under 35 U.S.C. § 119(a) of Australian provisional application 2016900442, filed Feb. 10, 2016, the entirety of which is hereby incorporated by reference.

BACKGROUND OF THE INVENTION

Field of the Invention

The present invention relates to improved PAK1-blocking compounds, methods and compositions for use in treatment of cancer and other PAK1-dependent diseases/disorders. More specifically, the present invention relates to PAK1-blocking esters of acidic PAK1-blockers used for treating a variety of PAK1-dependent diseases or disorders, use of these compounds in therapeutic methods and the manufacture of therapeutics, pharmaceuticals, medicaments and/or cosmetics as well as compositions containing these compounds. However, the invention is not limited to this particular field of use.

Description of the Related Art

Chemotherapies and radiation therapy are recognized as the mainstream approaches to the treatment of cancer. Such therapies however suffer a number of drawbacks. First, they generally come with severe side effects. Drugs used in chemotherapies characteristically damage and/or destroy cells that grow rapidly, such as cancer cells. Unfortunately, these treatments also affect rapidly growing normal cells such as blood cells in the bone marrow, cells in the hair follicles, and the cells that generate sperm in the testes. Secondly, cancer cells are able to develop resistance to the chemotherapeutic agents during the course of treatment. For example, the development of cisplatin resistance is a major source of failure in the treatment of non-small cell lung cancer.

In attempts to find alternative therapies, recent studies have established that PAKs, in particular PAK1 (RAC/CDC42-activated kinase 1), are essential for both growth and metastasis of many solid tumors, but non-essential for normal cell growth (1). PAK1 is found to be essential for growth of the so-called RAS cancers such as pancreatic and colon cancers, and breast cancers, which represent more than 70% of all human cancers. PAK1 is an oncogenic/pathogenic Ser/Thr protein kinase which is known to be responsible for a variety of diseases such as cancer and benign brain tumors such as neurofibromatosis (NF) and tuberous sclerosis (TSC), and many non-tumor diseases such as AIDS, malaria, viral/bacterial infections such as influenza, Alzheimer's Disease, Huntington's, diabetes (type 2), Parkinson's disease, inflammatory diseases such as asthma and arthritis, osteoporosis, obesity, hypertension, epilepsy, depression, learning disability, schizophrenia and autism associated with fragile X syndrome (FXS) as well as hyper-pigmentation and alopecia (hair loss), have also been identified as PAK1-dependent (1). Among the major substrates of PAK1 are the oncogenic/aging kinases RAF and LIM-kinase, an oncogenic/melanogenic transcription factor called beta-catenin, and the longevity transcription factor called FOXO. RAF, LIM-kinase and beta-catenin are activated by PAK1, while FOXO is inactivated by PAK1.

There is therefore sufficient evidence to implicate PAK1 as a target for the therapy of cancer and many other PAK1-dependent diseases/disorders. Thus, PAK1-blockers bear a potentially huge market value in both pharmaceutical and cosmetic industries. There no specific compound that directly inhibits only PAK1. This is largely because the 3-D structure of ATP-binding pocket in PAK1-3 are very similar to each other. Thus, an alternative approach would be to identify a few specific "kinase cascades" that activate only PAK1.

Several synthetic PAK1-blockers have been identified, but none have been approved by Food and Drug Administration for cancer therapy. Thus, patients suffering from PAK1-dependent diseases have to rely solely on a variety of herbal therapeutics such as caffeic acid phenethyl ester (CAPE) and curcumin, the main anticancer ingredients in propolis and Indian Curry, respectively, that block PAK1 without affecting normal cell growth (1).

Interestingly, there are a variety of "acidic" herbal compounds that indicate ability to block the oncogenic/aging kinase PAK1 including caffeic acid (CA) and artepillin C (ARC) (3,5-diprenyl-4-hydroxycinnamic acid) from propolis, ursolic acid (UA), and rosmarinic acid (RA) from Rosemary leaves. The major drawback for their clinical application is poor cell permeability and bioavailability (absorption through the intestine) in vivo.

Poor bioavailability (water-insolubility) is a big problem associated with many natural PAK1-blockers. In vitro indicators suggest efficacy as PAK1 blockers, but the human body does not absorb sufficient amounts for them to be effective. Curcumin, Resveratrol, Honokiol (from *Magnolia* bark) all appear, but unless sufficient amounts are absorbed, they will not provide an effective therapy of PAK1 diseases/disorders.

Therefore, there is a recognized need in the art for PAK1 blockers with improved cell permeability and bioavailability for treatment of cancer or any PAK1 dependent diseases or disorders. Particularly, the previous art is deficient in this aspect. The present invention fulfills this long-standing need and desire in the art.

SUMMARY OF THE INVENTION

The present invention is directed to a PAK1-blocking compound. The PAK1-blocking compound having a chemical structure Formula I The $R_1$ substituent may be the decarboxylated acidic PAK1 blocker. The $R_2$ substituent may be an aromatic group. The compound may be a pharmaceutically acceptable salt of the compound described above.

The present invention also is directed to a pharmaceutical composition. The composition comprises the PAK1-blocking compound described supra, and a pharmaceutically acceptable carrier.

The present invention is directed further to a method for treating PAK1 dependent diseases or disorders in a subject in need thereof. The method comprises the step of administering to the subject a therapeutically effective amount of the PAK1-blocking compound described herein.

The present invention is directed further still to a method for synthesizing a PAK1-blocking ester or pharmaceutically acceptable salt thereof described above. The method comprises the steps of esterifying a PAK1-blocking starting material comprising a carboxylic acid with an alcohol, and treating the esterified PAK1 blocking starting material with an aromatic azide to generate a 1,2,3-triazolyl derivative.

The present invention is directed further still to a PAK1 blocking ester or a pharmaceutically acceptable salt thereof. The PAK1 blocking ester or the pharmaceutically acceptable salt is synthesized by the esterification method described herein.

The present invention is directed further still to a method for treating a PAK1 dependent disease or disorder in a subject in need thereof. The method comprises a step of administering to the subject, in a pharmaceutically acceptable carrier, a therapeutically effective amount of the PAK1-blocking ester or a pharmaceutically acceptable thereof described supra.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

As used herein, in the specification the term "a" or "an" may mean one or more. As used herein in the claim(s), when used in conjunction with the word "comprising", the words "a" or "an" may mean one or more than one.

As used herein, the term "another" or "other" may mean at least a second or more of the same or different claim element or components thereof. Similarly, the word "or" is intended to include "and" unless the context clearly indicates otherwise.

As used herein, the term "comprise" or variations such as "comprises" or "comprising" are used in an inclusive sense, i.e. to specify the presence of the stated features but not to preclude the presence or addition of further features in various embodiments of the invention.

As used herein, the terms "including" or "which includes" or "that includes" is also an open term that also means including at least the elements/features that follow the term, but not excluding others. Thus, including is synonymous with and means comprising.

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "$IC_{50}$" refers to the concentration of a particular compound required to inhibit 50% of a specific biological activity. $IC_{50}$ can be measured, inter alia, as is in the examples and in Table 1.

As used herein, the term "treat" and variants thereof refer to a therapeutic intervention with an effective amount of a PAK1-blocker of formula (I). For example, the term includes within its scope therapeutic intervention to have one or more of the following outcomes: (i) inhibit or prevent the growth of a primary tumour in a subject, including reducing the growth of the primary tumour after resection; (ii) inhibit or prevent the growth and formation of one or more secondary tumours in a subject; (iii) improve the life expectancy of the subject as compared to the untreated state; and (iv) improve the quality of life of the subject as compared to the untreated state.

As used herein, the term "inhibit" refers to a reduction in the progress of a process, including any one or more of the start, rate, probability, continuation or termination of a process.

As used herein, the term "cancerous cell" refers to a cell that is immortalized and whose growth is not contact inhibited by other cells. A cancerous cell may also no longer show a dependence on exogenous growth factors and/or anchorage dependent growth.

As used herein, the term "biological system" refers to any multi-cellular system and includes isolated groups of cells to whole organisms. For example, the biological system may be cells in tissue culture, a tissue or organ, or an entire human subject suffering the effects of undesired or uncontrolled growth of cancerous cells.

As used herein, the term "therapeutically effective amount" or "effective amount" of a compound refers to an amount of compound that is effective to prevent, alleviate or ameliorate symptoms of disease or prolong the survival of the subject being treated. Determination of a therapeutically effective amount is within the skill in the art.

As used herein, the term "EDs" or "effective doses" relates to the dose(s) of compound, which, when administered according to the desired dosing regimen, provides the desired therapeutic activity. Dosing may occur at the intervals of hours, days, weeks, months or years, or continuously over one of these periods. Typically the suitable dosages may lie within the range of about 1 μg to 500 mg per kg of body weight per dosage.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" or "in another embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of the Invention are hereby expressly incorporated into this detailed description with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination. In the description provided herein, numerous specific details are set forth. However, it is understood that embodiments of the invention may be practiced without these specific details. In other instances, well-known methods, structures and techniques have not been shown in detail in order not to obscure an understanding of this description.

In one embodiment of the present invention, there is provided a PAK1-blocking compound having a chemical structure Formula I:

(I)

wherein $R_1$ is a decarboxylated acidic PAK1 blocker; and $R_2$ is an aromatic group; or a pharmaceutically acceptable salt thereof.

In this embodiment, the exemplary $R_1$ includes but is not limited to decarboxylated form of artepillin C (ARC), caffeic acid (CA), R-ketorolac, captopril, CDDO/TP151, MFF, Mimosinyl-Phe-Phe, Crocetin monoester, CX-4945, rosmarinic acid (RA), or nicotinic acid (Niacin). Representative example of $R_2$ include but are not limited to ortho-phenol, ortho-methoxy benzene, ortho-aniline, ortho-arginine phenyl ester, or ortho-aminohexyl benzene.

In another embodiment of the present invention, there is provided a pharmaceutical composition comprising the PAK1-blocking compound described supra. Preferably, the concentration of the PAK1-blocking compound in the composition is from about 5 nM to about 250 nM.

In yet another embodiment of the present invention, there is provided a method for treating a PAK1 dependent disease or disorder in a subject in need thereof comprising a step of administering to the subject, a therapeutically effective amount of the PAK1-blocking compound described above.

In this embodiment, the cell permeability of the PAK1 blocking compound has a cell permeability about 100 fold to about 500 fold of an acidic PAK1 blocker. Examples of PAK1 dependent disease or disorder may include but is not limited to solid tumors, Alzheimer's disease, Parkinson's disease, Huntington's disease, arthritis, asthma, multiple sclerosis, stomach ulcer, malaria, AIDS, diabetes (type 2), hypertension, epilepsy, schizophrenia, autism, depression, obesity, hyper-pigmentation, alopecia, pain and osteoporosis or a combination thereof. In one embodiment, the PAK1 dependent disease may be cancer. Exemplary cancers include but are not limited to pancreatic cancer, colon cancer, breast cancer, prostate cancer, lung cancer, brain cancer (glioma), neurofibromatosis type I or neurofibromatosis type II, tuberous sclerosis complex, multiple myeloma (MM) or a combination thereof.

In yet another embodiment of the present invention, there is provided a method for treating a cancer in a subject having an increased resistance to a conventional anti-cancer therapy, comprising a step of administering to the subject, a therapeutically effective amount of the PAK1-blocking compound as described supra.

In yet another embodiment of the present invention, there is provided a method for synthesizing a PAK1-blocking ester or a pharmaceutically acceptable salt thereof, comprising the steps of esterifying a PAK1-blocking starting material comprising a carboxylic acid with an alcohol; and treating the esterified PAK1 blocker with an aromatic azide to generate a 1,2,3-triazolyl derivative. In this embodiment, the PAK1-blocking starting material comprises artepillin C, caffeic acid, R-ketorolac, captopril, CDDO/TP151, Mimosinyl-Phe-Phe, Crocetin monoester, CX-4945, rosmarinic acid, or nicotinic acid.

In this embodiment, the PAK1-blocking ester has a chemical structure Formula I:

(I)

wherein $R_1$ is a decarboxylated form of artepillin C, caffeic acid, R-ketorolac, captopril, CDDO/TP151, Mimosinyl-Phe-Phe, Crocetin monoester, CX-4945, rosmarinic acid, or nicotinic acid; and $R_2$ is an aromatic group comprising ortho-phenol, ortho-methoxy benzene, ortho-aniline, ortho-arginine phenyl ester, or ortho-aminohexyl benzene.

In yet another embodiment of the present invention, there is provided the blocking ester or pharmaceutically acceptable salt thereof synthesized by the method described supra.

In yet another embodiment of the present invention, there is provided a pharmaceutical composition comprising the PAK1-blocking ester or a pharmaceutically acceptable salt thereof described supra and a pharmaceutically acceptable carrier.

In yet another embodiment of the present invention, there is provided a method for treating a PAK1 dependent disease or disorder in a subject in need thereof comprising administering to the subject in a pharmaceutically acceptable carrier, a therapeutically effective amount of the PAK1-blocking ester or the pharmaceutically acceptable salt thereof described supra.

In this embodiment, the exemplary PAK1 dependent disease or disorder includes but is not limited to a cancer, Alzheimer's disease, Parkinson's disease, Huntington's disease, arthritis, asthma, multiple sclerosis, stomach ulcer, malaria, AIDS, diabetes (type 2), hypertension, epilepsy, schizophrenia, autism, depression, obesity, hyper-pigmentation, alopecia (hair loss), pain and osteoporosis or a combination thereof. In this embodiment, the cancer may be pancreatic cancer, colon cancer, breast cancer, prostate cancer, lung cancer, brain cancer (glioma), neurofibromatosis type I or neurofibromatosis type II, tuberous sclerosis complex, multiple myeloma (MM) or a combination thereof.

Provided herein are esters of acidic PAK1 blockers found to improve both cell permeability and bioavailability of these PAK1 blockers. In cells, PAK1 requires not only RAC/CDC42, the oncogenic GTP-dependent proteins (G proteins), but also at least three distinct oncogenic Tyr-kinases called ETK, FYN and JAK2, as well as a Ser/Thr kinase called CK2 (casein kinase 2) and a few other adaptor proteins such as PIX and NCK, for full activation (1). In other words, if one or two of these upstream activators of PAK1 is inhibited directly by a "PAK1-blocker", the oncogenic activity of PAK1 is fully blocked. For instance, AG879/GL-2003 directly inhibits ETK, while PP1 directly inhibits FYN. ETK and FYN independently activate PAK1 but in a complementary manner. Thus, if these two compounds are combined, PAK1 could be fully blocked in cells, and the growth of most of (PAK1-dependent) solid tumors such as pancreatic cancer could be completely suppressed in mouse model without any side effect (2). However, PP1 is water-insoluble, and cannot be used for clinical application. The PAK1-blocking ester compounds of formula (1) improve cell permeability many fold without any substantial decrease in water solubility. As a result, the active compound has increased bioavailability within cells and can diffuse through the blood brain barrier so as to be effective in therapy of brain tumors such as gliomas and tumors associated with neurofibromatosis type I or neurofibromatosis type II, tuberous sclerosis complex, whose proliferation also requires PAK1 (1). This represents a substantial contribution and improvement to the therapy of PAK1-dependent diseases.

The PAK1 blockers comprise PAK1-blocking esters of formula (I) or pharmaceutically acceptable salts thereof, for use in substantially blocking abnormal activation of PAK1 in affected cells. The compounds have the chemical structure as shown below although it is contemplated that structurally similar analogs and derivatives, such as, but not limited to, homologs are functionally similar:

(I)

Preferably $R_1$ is a decarboxylated form of any acidic PAK1 blockers, both synthetic and herbal, such as, but not limited to, artepillin C (ARC), caffeic acid (CA), R-ketorolac ((R)-(+)-5-benzoyl-2,3-dihydro-1H-pyrrolizine-1-carboxylic acid), captopril ((2S)-1-[(2S)-2-methyl-3-sulfanyl-propanoyl]pyrrolidine-2-carboxylic acid), CDDO/TP151 (Cyano-derivative of Oleanolic acid), Mimosinyl-Phe-Phe (MFF), Crocetin monoester (beta-D-glucosyl crocetin), CX-4945 (Silmitasertib), rosmarinic acid (RA), and nicotinic acid (Niacin). Preferably $R_2$ is any aromatic group such as, but not limited to, ortho-phenol, ortho-methoxy benzene, ortho-aniline, ortho-arginine phenyl ester, and ortho-amino-hexyl benzene.

The present invention provides a related composition of the PAK1-blocking ester of structural formula (1) including a pharmaceutically acceptable salt thereof, together with at least one pharmaceutically or cosmetically acceptable adjuvant, carrier or diluent, wherein the PAK1-blocking ester is present in a therapeutically effective amount to provide anti-cancer activity or cell permeability of the compound greater than its original moiety by about 100 to 6000 fold, and the $IC_{50}$ is between about 5-250 nM.

The present invention also provides a pharmaceutical composition including a compound of structural formula (1) or a pharmaceutically acceptable salt thereof, together with at least one pharmaceutically or cosmetically acceptable adjuvant, carrier, exipient, or diluent as described herein and/or as known and standard in the art. The pharmaceutical composition may be used in therapeutic regimens, such as for treating pathophysiological conditions associated with PAK1 and other PAK1 diseases and disorders.

The compounds of the invention may be in crystalline form, either as the free compounds or as solvates (e.g., hydrates), and it is intended that both forms are within the scope of the present invention. Methods of solvation are generally known within the art.

It has been surprisingly found that the compounds of formula (1) in the present invention have improved at least anti-cancer, anti-melanogenic and anti-alopecia activities in cell culture mainly by a robust increase in cell-permeability by 100-1000 fold, depending on target cells and original sources such as ARC, CA and R-ketorolac, while at the same time retain or even boost the PAK1-blocking activity. Compared to acidic PAK1-blockers such as ARC, CA, and R-ketorolac, the cell permeability of structural compounds of formula (1), and their bioavailability, increases at least 100 fold. This means that lower concentrations of formula (1) are required within cells to achieve a therapeutic effect.

Thus, the present invention provides methods for treating pathophysiological conditions associated with PAK1, such as cancer and other PAK1 dependent diseases. The method comprises administering an effective or therapeutic amount of a compound of formula (I) for blocking the activation of PAK1. PAK1 dependent or associated diseases may include any one or more of a solid tumor, Alzheimer's disease, Parkinson's disease, Huntington's disease, inflammatory diseases, such as arthritis, asthma, multiple sclerosis and stomach ulcer and an infectious disease, such as malaria and AIDS, type 2 diabetes, hypertension, epilepsy, schizophrenia, autism, depression, obesity, disorders such as hyper-pigmentation, alopecia (hair loss), pain and osteoporosis.

Further, the present invention provides a method of treating a subject with a disorder selected from brain tumors and other PAK1-dependent diseases such as Alzheimer's disease. An effective amount of a compound represented by structural formula (1) or a pharmaceutically acceptable salt thereof upon administration is able to diffuse across the blood brain barrier and thus become available for brain tumours and other PAK1-dependent brain diseases.

Further still, the present invention provides a method of treating a subject with a PAK1-dependent disorder such as alopecia, hyper-pigmentation and osteoporosis. An effective amount of a compound represented by structural formula (1) or a pharmaceutically/cosmetically acceptable salt thereof for inactivating PAK1 is administered to the subject or brought into contact with an affected area on the subject.

Further still, the present invention provides a method of treating PAK1 dependent diseases or conditions by achieving a therapeutic blood concentration in the subject. An effective amount of the compound(s) or compositions described herein is administered over a predetermined period using predetermined dosages.

Further still, the present invention also provides a method of improving skin-whitening and hair growth-promoting by administering a therapeutically effective amount of a compound of formula (1). It is understood that PAK1 is responsible for the ageing process and clearly shortens the lifespan, induction of melanogenesis in skin cells, and hair loss (alopecia). The improved cell-permeable 1,2,3-triazoyl derivatives according to a compound of formula (1), reduces PAK1 activity and can therefore be useful for skin-whitening or hair growth-promoting cosmetics as well.

The present invention also provides a method for inhibiting formation and/or growth of a solid tumor in a subject. The subject is exposed to or has administered to an amount of a compound of formula (1) or pharmaceutically acceptable salt wherein the cell permeability of the compound is higher than its original compound by 100-500 folds, and the IC50 (concentration for 50% inhibition of cancer cell growth) is 25-250 nM (see Table 1). The solid tumour may include pancreatic cancer, colon cancer, breast cancer, prostate cancer, lung cancer, brain cancer (glioma), NF (types I and II), TSC, and multiple myeloma (MM).

Thus, the present invention also provides a method of treating a subject with solid tumors. A therapeutically effective amount of the compound(s) described herein are administered to the subject, wherein the anti-cancer activity or cell permeability of the compound is higher than its original compound by 100-6000 fold, and the IC50 (concentration for 50% inhibition of cancer cell growth) is 5-250 nM.

A tumor may be a primary tumor or a secondary or metastatic tumor. Thus, the present invention also is useful to inhibit the formation and growth of a primary tumour, and/or be used to inhibit the formation and/or growth of metastases in the subject.

The present invention also provides methods for preventing and/or treating a PAK1 dependent disease in a subject that has an increased resistance to a conventional anti-cancer therapy and for reducing the resistance of cancers to a conventional chemo/radiation-therapy. The subject or a cancerous cell is exposed to or contacted with an effective amount or dose of a compound(s) or composition(s) or pharmaceutically acceptable salts thereof described herein.

The inhibition of growth and metastasis of the cancerous cell in the various embodiments of the present invention may take any form of inhibition of proliferation of the cell. For example, the inhibition of proliferation may involve inhibiting the ability of a cell to begin proliferating, continue proliferating or reducing the probability that a particular cell will begin or continue proliferating. A level of inhibition of the growth of a cancerous cell may be assessed by a method known in the art. For example, for a cancerous cell in vitro, the growth of the cancerous cell may be determined by a suitable proliferation assay. For a cancerous cell present in vivo, the growth of the cancerous cell may be determined for example by a suitable imaging method known in the art. Those skilled in the art will appreciate that the invention described herein is susceptible to modifications and variations other than those specifically described.

Thus, provided herein are methods for treating a cancer or a variety of other PAK1-dependent diseases. The compound(s) or compositions or pharmaceutically acceptable salts described herein are administered in a therapeutically effective amount or effective dose at predetermined intervals over a predetermined period, wherein the amount is substantially maintained within a predetermined therapeutic range effective for inactivating PAK1.

The compounds of formula (1) or pharmaceutically acceptable salts thereof are useful in the manufacture of a pharmaceutical composition or other therapeutic agent, drug or medicament for promoting the activity of a PAK1-blocker in a therapeutic treatment regimen for cancer and other PAK1 dependent diseases in a subject. For example, these compounds, compositions, agents and medicaments are useful in treating benign, but lasting life-long, tumors such as NF and TSC in a subject and for preventing and/or treating a cancer in a subject having an increased resistance to an anti-cancer therapy.

Suitable dosage amounts and dosing regimens using compounds of formula (1) can be determined by attending physician(s) and may depend on the particular conditions or the nature of diseases/disorders being treated, and the severity of condition and the general age, health and body weight of the subject. Preferably the method comprises administering a compound of formula (1) to a patient in an amount effective to treat PAK1-dependent diseases.

Dosing may occur at the intervals of hours, days, weeks, months or years, or continuously over one of these periods. Typically the suitable dosages may lie within the range of about 1 ug to 500 mg per kg of body weight per dosage. The composition can be administered according to a predetermined regimen depending on the above factors, severity of condition being treated, mode of administration, and strength of preparation.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration. It may be given as one or more bolus injections or as a continuous infusion.

The compound of formula (1) can be administered internally such as injection (intravenously, intramuscularly, subcutaneously, parenterally) orally, intranasally, inhalation, transdermal, topical, sublingually. Compositions of the present invention suitable for oral administration may be presented as discrete units such as capsules, sachets or tablets, pills, powder, granule, each containing a predetermined amount of the active ingredient; as a powder or granule; as a solution or suspension in an aqueous or non-aqueous liquid; or an oil-in-water/water-in-oil liquid emulsion. The active ingredient may also be presented as a bolus, electuary, ointment, cream or paste for topical pharmaceutical/cosmetic treatment.

Tablets and capsules represent desirable oral dosage forms. Tablets coated or otherwise compounded to provide a prolonged, controlled release therapeutic effect. The tablet can also include a protective coat such as an enteric layer which resists degradation in the stomach and permits the inner component to pass substantially intact into the duodenum.

The compounds of the invention are administered to the subject in therapeutic/treatment effective doses (EDs). As used herein, the therapeutic/treatment effective doses are intended to include at least partially attaining desired effect, or delaying the onset of, or inhibiting the progression of, or halting or reversing altogether the onset or progression of particular PAK1-dependent diseases/disorders such as pancreatic/colon cancer, NF and AD (Alzheimer's disease) to be treated.

The present invention further provides a method for preparing synthetic derivatives of PAK1-blockers according to the compounds of formula (1). The compounds in the present invention can be prepared by a reaction sequence called "Copper-catalyzed click chemistry". Preferably in a first step, a carboxylic acid group-containing PAK1-blocker starting material is esterified using a suitable alcohol, and the resulting ester compound is treated with a select aromatic azide yielding the corresponding 1,2,3-triazolyl derivative.

The resultant 1,2,3-triazolyl derivatives of chemically synthesizable acidic PAK1-blockers such as artepillin C, caffeic acid, R-ketorolac, captopril, CDDO/TP151, Mimosinyl-Phe-Phe, crocetin and CX-4945, shows the higher cell permeability. Without being bound by theory, the presence of the water-soluble triazole ring coupling surprisingly increases the cell-permeability by 100-1000 fold, depending on target cells and original compounds, substantially without reducing the water-solubility. In other words, it is now clear from applicant's invention that the carboxylic group of these PAK1-blockers are not essential for their PAK1-blocking activity per se.

In principle, the acidity (negative charge) from a carboxylic group hampers efficient penetration through the "acidic" (phospholipid based) cell membranes. Accordingly, esterification of the carboxylic group by a select alcohol significantly improves cell permeability, as a CA ester called CAPE is 10 fold more potent (cell-permeable) than CA, while a select UA ester is 200 fold more potent than UA. Likewise, the compounds of formula (1) are rendered more positively charged and lipophilic (than the original "acidic" compounds), being more favourable to the cell-permeation, by the "click chemistry". The compounds of formula (1) are of a size sufficiently small to pass the Blood Brain Barrier, and therefore useful for treating brain tumours and other neuronal diseases such as Alzheimer's disease.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Figure 1:
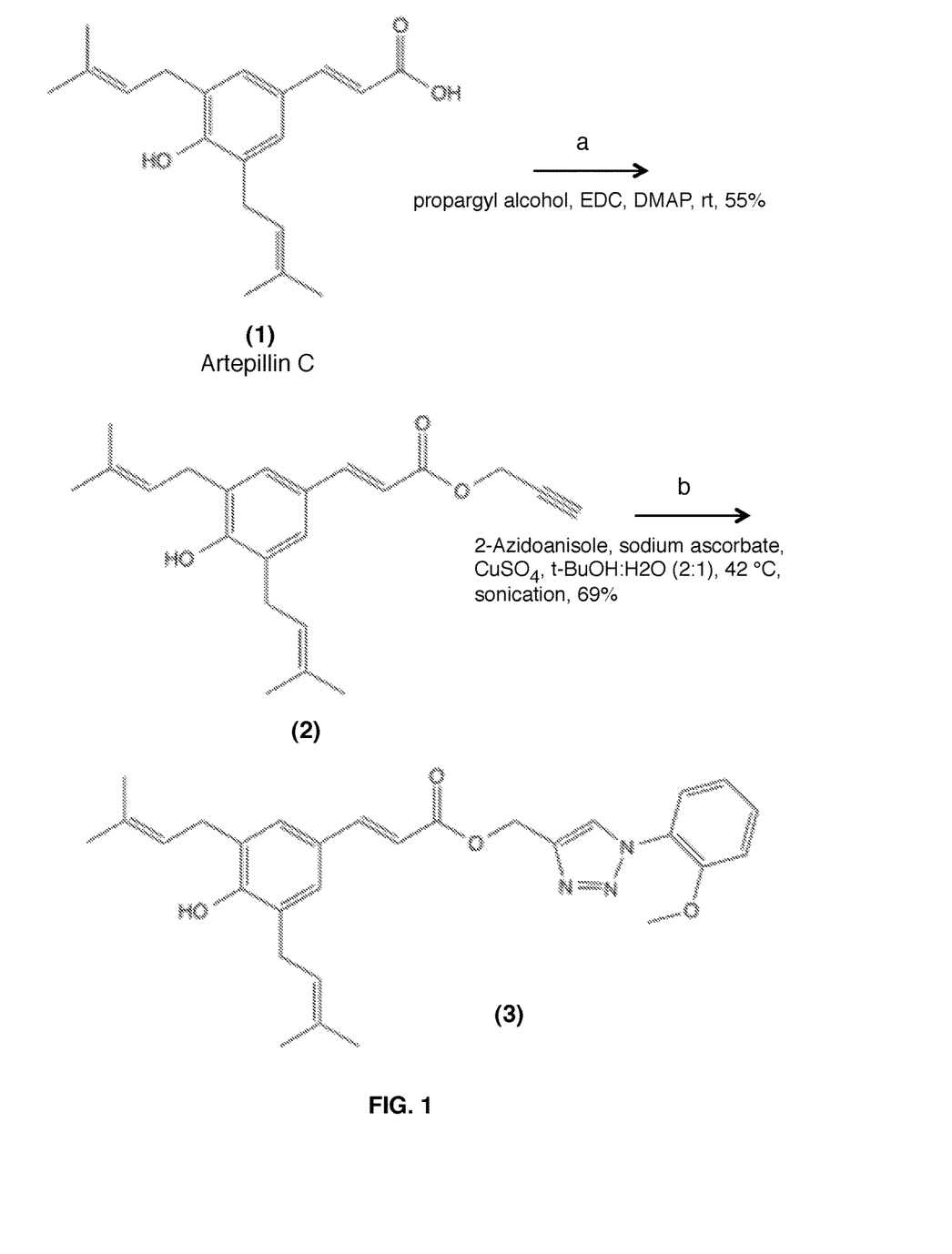
FIG. 1 is a schematic representation of a reaction sequence for preparing a 1,2,3-Triazolyl derivative of ARC (AzoARC or PRC-15A).

Preparation of 1,2,3-Triazolyl Derivative of ARC: Compound 3 in Scheme 1 (FIG. 1)

Step a:

To solution of compound 1 (ARC, 161 mg, 536 mmol) in Propargyl alcohol (6 ml) at 0° C., EDC (100 ul, 567 mmol) and DMAP (17 mg, 139 mmol) were added. The reaction mixture was stirred at room temperature and monitored by TLC till its completion in around a day. The crude mixture was then evaporated. The residue was purified through flash silica gel column chromatography (n-haxane:EtOAc=3:1) to give pure 2 (100 mg, 295 mmol, 55% yield) as a pale yellow solid. $^1$H-NMR (400 MHz, CDCl$_3$) d=7.66 (d, J=15.9 Hz, 1H), 7.17 (s, 2H), 6.29 (d, J=15.9 Hz, 1H), 5.30 (t, J=7.30 Hz, 2H), 4.79 (d, J=2.27 Hz, 2H), 3.33 (d, J=7.14 Hz, 4H), 2.49 (t, J=2.44 Hz, 1H), 1.77 (d, J=8.76 Hz, 12H).

Step b:

To solution of compound 2 (52 mg, 154 mmol) in t-BuOH:H$_2$O (2:1, 4 ml), Sodium ascorbate (6 mg, 30.3 mmol) and CuSO$_4$ (4 mg, 25.1 mmol) were added at room temperature. To this mixture, 2-Azidoanisole (0.5 M solution, 310 ul, 155 mmol) was added and the reaction mixture was sonicated at 42° C. till its completion around 7 hours, monitored by TLC. The crude mixture was extracted with ethylacetate (3×20 ml) and organic layer was washed with water and brine, then dried over sodium sulfate and purified through flash silica gel column chromatography (n-haxane:EtOAc=3:1) to give pure 3 (52 mg, 107 mmol, 69% yield) as a pale yellow solid. $^1$H-NMR (400 MHz, CDCl$_3$) d=8.20 (s, 1H), 7.77 (d, J=7.79 Hz, 1H), 7.63 (d, J=16.1, 1H), 7.42 (t, J=7.78 Hz, 1H), 7.15 (s, 2H), 7.12-7.07 (m, 2H), 6.30 (d, J=15.6 Hz, 1H), 5.42 (s, 2H), 5.28 (t, J=6.49 Hz, 2H), 3.89 (s, 3H), 3.32 (d, J=7.27 Hz, 4H), 1.76 (d, J=7.27, 12H). HRMS calcd for C$_{29}$H$_{34}$N$_3$O$_4$ (M+H)$^+$ m/z 488.2549. found m/z 488.2586.

EXAMPLE 2

Figure 2:
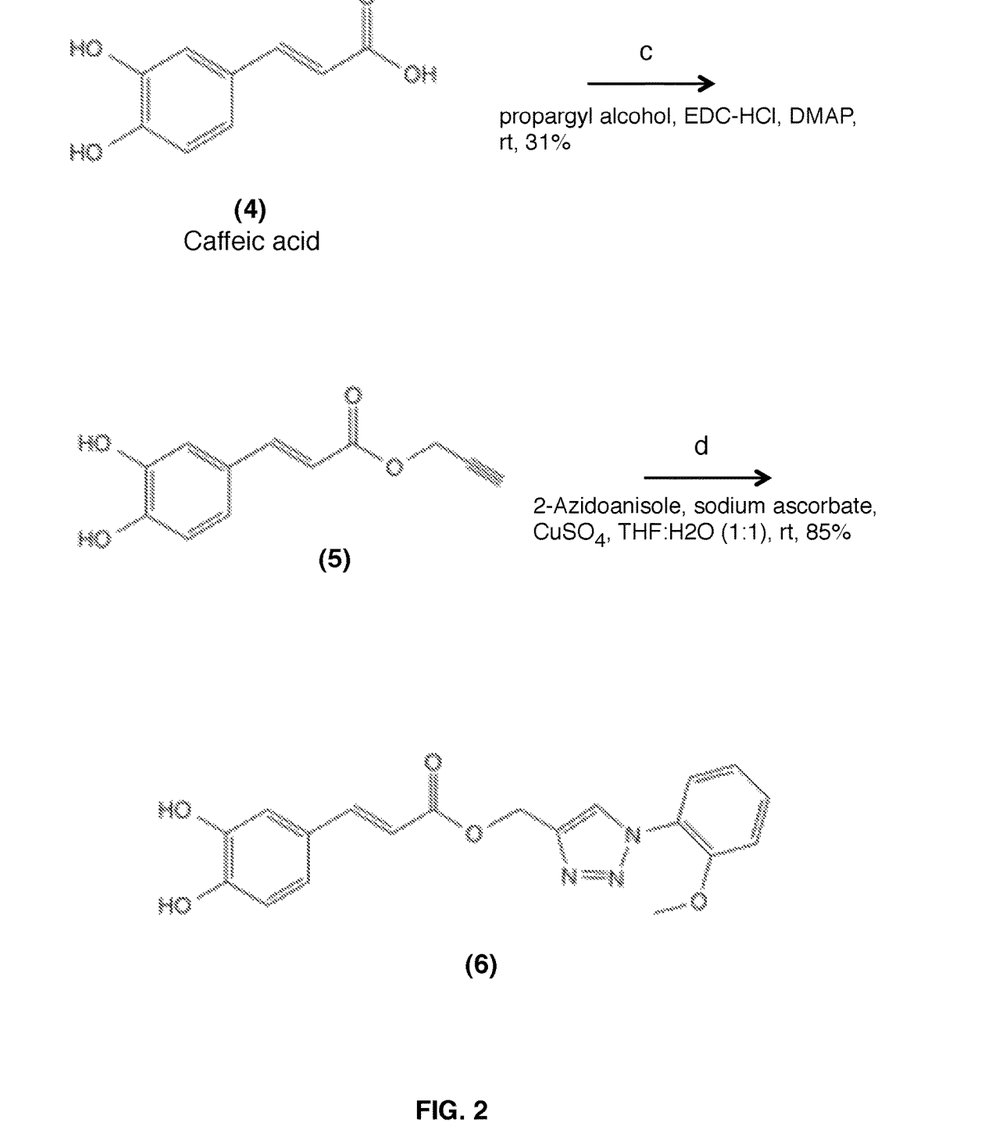
FIG. 2 is a schematic representation of a reaction sequence for preparing a 1,2,3-Triazolyl derivative of CA (AzoCA or PRC-15C).

Preparation of 1,2,3-Triazolyl Derivative of CA: Compound 6 in Scheme 2 (FIG. 2)

Step c:

To solution of compound 4 (CA, 382 mg, 2.12 mmol) in DMF (3 ml) at 0° C., EDC HCl (423 mg, 2.21 mmol) and DMAP (72 mg, 589 mmol) were added. To this solution, Propargyl alcohol (400 ml, 6.87 mmol) was added and the reaction mixture was stirred at room temperature for 17 hours. After quenching the reaction with cooled HCl aq. (0.5 M, 20 ml), crude product was extracted with ethylacetate: n-hexane (1:1) three times. Organic layer was washed with aqueous solution of saturated sodium hydrogen carbonate and brine, and then dried over sodium sulfate. This crude product was purified through flash silica gel column chromatography (n-haxane:EtOAc=1:1) to give pure 5 (143 mg, 655 mmol, 31% yield) as a milky white solid. $^1$H-NMR (400 MHz, CDCl$_3$) d=7.62 (d, J=16.1 Hz, 1H), 7.07 (d, J=2.08 Hz, 1H), 7.00 (d, J=8.00 Hz, 1H), 6.87 (d, J=8.30 Hz, 1H), 6.27 (d, J=16.1 Hz, 1H), 4.80 (d, J=2.60 Hz, 2H), 2.50 (t, J=2.60 Hz, 1H).

Step d:

To solution of compound 5 (130 mg, 595 mmol) in THF:H$_2$O (1:1, 4 ml), Sodium ascorbate (61 mg, 308 mmol) and CuSO$_4$ (17 mg, 107 mmol) were added at room temperature. To this mixture, 2-Azidoanisole (0.5 M solution, 1.20 ml, 600 mmol) was added and the reaction mixture was stirred at room temperature till its completion around 5 hours. The crude mixture was extracted with ethylacetate (3×20 ml). Organic layer was washed with water and brine, and then dried over magnesium sulfate. Without column chromatography, the pure 6 (185 mg, 504 mmol) was obtained in 85% yield as a milky white powder. $^1$H-NMR (400 MHz, CD$_3$OD) d=8.37 (s, 1H), 7.64 (d, J=8.04 Hz, 1H), 7.58 (d, J=15.6 Hz, 1H), 7.50 (t, J=7.92 Hz, 1H), 7.23 (d, J=8.30 Hz, 1H), 7.12 (t, J=7.79 Hz, 1H), 7.02 (d, J=2.08 Hz, 1H), 6.93 (d, J=8.04 Hz, 1H), 6.75 (d, J=8.30 Hz, 1H), 6.28 (d, J=15.6 Hz, 1H), 5.35 (s, 2H), 3.89 (s, 3H). HRMS calcd for C$_{19}$H$_{18}$N$_3$O$_5$ (M+H)$^+$ m/z 368.1246. found m/z 368.1250.

EXAMPLE 3

Figure 3:
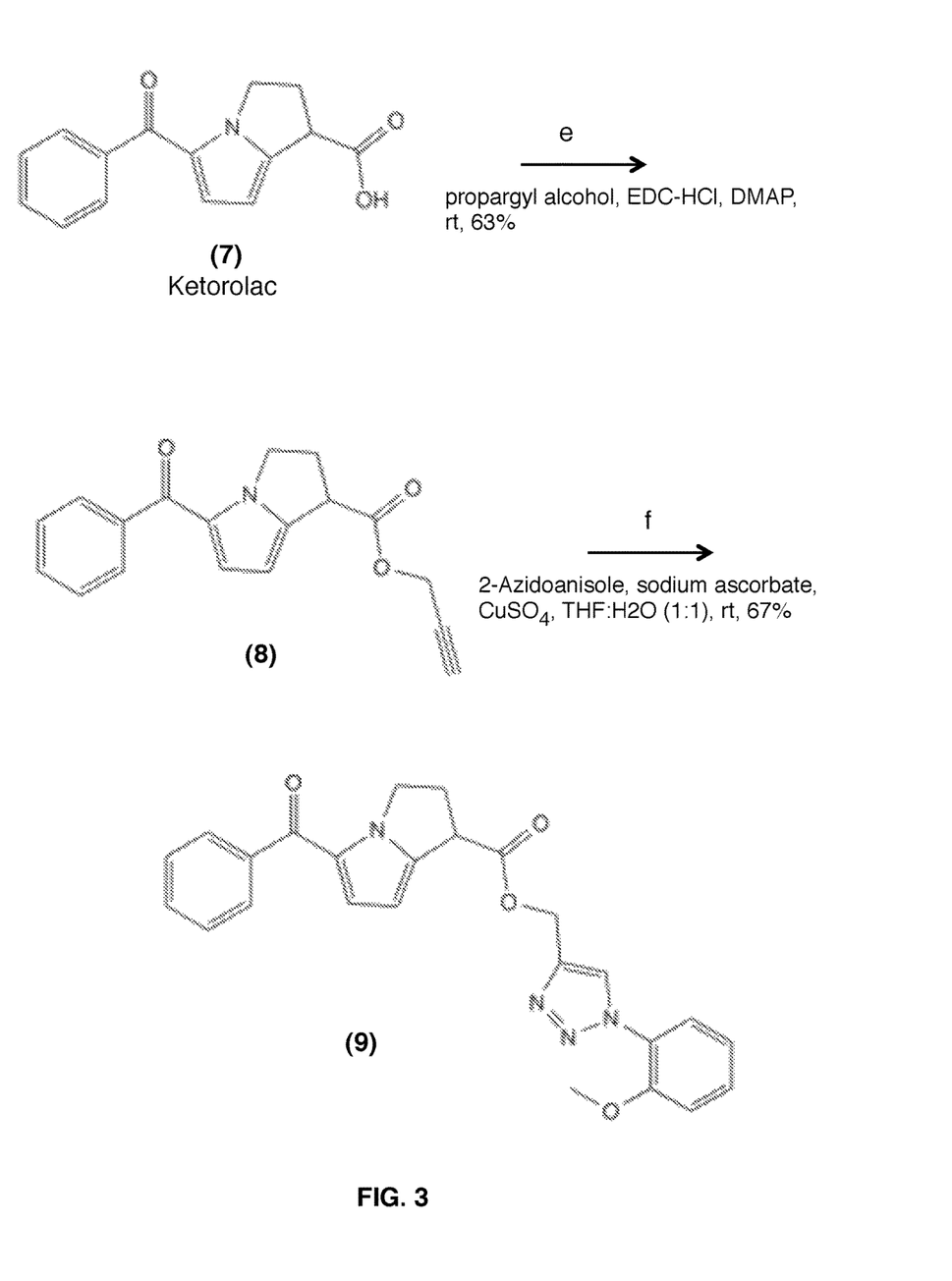
FIG. 3 is a schematic representation of a reaction sequence for preparing 1,2,3-Triazolyl derivative of R-ketorolac (AzoKeto or PRC-15K).

Preparation of 1,2,3-Triazolyl Derivatives of R-Ketorolac: Compound 9 in Scheme 3 (FIG. 3)

Step e:

To solution of compound 7 (racemic 50/50 mixture of R and S forms of Ketorolac, 202 mg, 794 mmol) in DMF (3 ml) at 0° C., EDC HCl (156 mg, 813 mmol) and DMAP (60 mg, 491 mmol) were added. To this solution, Propargyl alcohol (200 ml, 3.43 mmol) was added and the reaction mixture was stirred at room temperature for 5 hours. After quenching the reaction with cooled HCl aq. (0.5 M, 20 ml), crude product was extracted with ethylacetate:n-hexane (1:1) three times. Organic layer was washed with aqueous solution of saturated sodium hydrogen carbonate and brine, and then dried over sodium sulfate. This crude product was purified through flash silica gel column chromatography (n-haxane:EtOAc=1:1) to give pure 8 (147 mg, 501 mmol, 63% yield) as a pale yellow oil. $^1$H-NMR (400 MHz, CDCl$_3$) d=7.81 (d, J=7.79 Hz, 2H), 7.52 (d, J=7.26 Hz, 1H), 7.44 (d, J=7.26 Hz, 2H), 6.81 (d, J=3.63 Hz, 1H), 6.13 (d, J=4.67 Hz, 1H), 4.76 (d, J=2.60 Hz, 2H), 4.61-4.55 (m, 1H), 4.48-4.41 (m, 1H), 4.14-4.09 (q, 1H), 2.99-2.90 (m, 1H), 2.86-2.77 (m, 1H) 2.50 (t, J=2.20 Hz, 1H).

Step f:

To a solution of compound 8 (190 mg, 648 mmol) in THF:H$_2$O (1:1, 4 ml), Sodium ascorbate (65 mg, 328 mmol) and CuSO$_4$ (21 mg, 131 mmol) were added at room temperature. To this mixture, 2-Azidoanisole (0.5 M solution, 1.30 ml, 650 mmol) was added and reaction mixture was stirred at room temperature till its completion. The crude mixture was extracted with ethylacetate (3×20 ml). Organic layer was washed with water and brine, and then dried over magnesium sulfate and purified through flash silica gel column chromatography (n-haxane:EtOAc=1:1) to give pure 9 (191 mg, 432 mmol, 85% yield) as a light grey oil. $^1$H-NMR (400 MHz, CDCl$_3$) d=8.15 (s, 1H), 7.80-7.76 (m, 3H), 7.51 (t, J=7.42 Hz, 1H), 7.45-7.40 (m, 3H), 7.12-7.06 (m, 2H), 6.78 (d, J=3.60 Hz, 1H), 6.07 (d, J=4.11 Hz, 1H), 5.40 (s, 2H), 4.60-4.53 (m, 1H), 4.46-4.40 (m, 1H), 4.14-4.08 (m, 1H), 3.87 (s, 3H), 2.98-2.09 (m, 1H), 2.85-2.75 (m, 1H). HRMS calcd for $C_{25}H_{23}N_4O_4$ (M+H)$^+$ m/z 443.1719. found m/z 443.1737.

It is noted that the FDA-approved anti-inflammatory/analgesic compound 7 (ketorolac) possesses an asymmetric center, and therefore exists in two distinct stereoisomers (R and S forms), in which only R-form is active as a RAC-inhibitor/PAK1-blocker, while S-form is active as a COX-2 inhibitor (3). Fortunately, however, the "inactive" S-form does not interferes with the PAK1-blocking activity of R-form. Thus, the commercially available ketorolac used clinically is a 50/50 racemic mixture, and IC$_{50}$ of the racemic mixture against the growth of human cancer cells is 13 mM (our unpublished observation). Consequently, both compounds 8 and 9 also exist in a 50/50 racemic mixture, and the IC$_{50}$ of the compound 9 is around 24 nM, being more than 500 times potent as much as the compound 7 (racemic mixture of ketorolac), as described in detail herein. Furthermore, it was shown that PAK1 is essential for COX-2 gene expression which is also required for the growth of cancer cells or melanogenesis. Thus, compound 9 blocks the oncogenic/melanogenic RAC-PAK1-COX-2 signalling through two distinct (independent) routes, and it is most unlikely that the pharmacological/cosmetic action of compound 9 is severely hampered by any single drug-resistant mutation.

EXAMPLE 4

Preparation of 1,2,3-Triazolyl Derivative of Captopril (Azocapto or PRC 15-CP), Preparation of 1,2,3-Triazolyl Derivative of CDDO/TP151 (2-Cyano Derivative of Oleanolic Acid), 1,2,3-Triazolyl Derivative of Mimosinyl-Phe-Phe (AzoMFF or PRC-15M), 1,2,3-Triazolyl Derivative of Crocetin Monoester (AzoCro or PRC-15R), and 1,2,3-Triazolylderivative of CX-4945 (AzoCX or PRC-15X)

Starting materials are CDDO, MFF, Crocetin momoester and CX-4945. Briefly, in the first step, each carboxylic acid group-containing starting material was treated with propargyl alcohol (as shown in steps a, c and e), and in the following step the resulting compound (propargyl ester) was then treated with 2-Azidoanisole and CuSO$_4$ (as shown in steps b, d and f), yielding the corresponding triazolyl derivative.

EXAMPLE 5

Anti-Cancer Activity

Cell Lines

A. Cell Lines: Human lung cancer (A549) cells carrying an oncogenic K-RAS mutant or murine melanoma (B16F10) cells B. Cell seeding in 96 well plate: In culture medium D-MEM with or without 10% fetal bovine serum.

C. Inhibitor Stocks in DMSO (100 mM)

D. Trypan Blue Assay for Cell Viability/Growth (4): The most commonly used MTT assay for cell viability/growth is not feasible for cells treated with triazolyl derivatives, mainly because these compounds are reduced by mitochondrial reductase in viable cells, just like MTT, and converted to a purple compound which would clearly interfere with the colorimetry on which MTT assay depends. Thus, a more classic method called Trypan Blue exclusion assay should be used for determining cell viability/growth of cells treated with all triazolyl derivatives. In this assay, only dead cells are stained with Trypan Blue, while viable cells exclude this blue dye.

The assay was conducted as previously described. Briefly, A549 or B16F10 cells were seeded at 2×10$^4$ cells/well in 96 well plate for 24 hrs in the above medium, and then treated with one of the tested compounds in the same medium for 96 hrs. Cell were detached from the plate by a protease called accutase, and stained with Trypan blue, and the number of unstained (viable) cells was counted in a hemocytometer.

EXAMPLE 6

Anti-Melanogenic Activity

A. Cell line: Murine melanoma (B16F10) cells.

B. Cell seeding in 96 well plate: In culture medium D-MEM supplemented with 10% heat-activated FBS (fetal bovine serum) and 1% penicillin/streptomycin (10,000 U/mL and 100 μg/mL). 2×10$^4$ cells were seeded in each well of 96 well plate in the medium at 37° C. for 24 hrs in a humidified atmosphere containing 5% CO$_2$.

C. Inhibitor Stocks in DMSO (100 uM).

D. Trypan Blue assay for cell viability (4).

E. Melanin content Assay (4): The assay was performed as previously described. Cells were seeded in a 96-well plate at a density 5×10$^4$ cells/well in culture medium containing D-MEM supplemented with 10% FBS, 1% penicillin/streptomycin, and cultured for 24 hrs. Then, the cells were treated with a melanogenic stimulating hormone called α-MSH (100 nM), and treated with one of tested compounds for 48 hrs. After the medium was removed, cells were dissolved in 100 μL of 1 N NaOH. The mixture was heated at 90° C. for 1 hr, and the melanin content was estimated by reading the absorbance at 405 nm.

F. Tyrosinase Assay (4): Tyrosinase activity was determined as previously described with a slight modification. B16F10 cells (wild-type or the transfectants) were plated at a density of 2×10⁴ cells/well, and after 24 hrs of pre-culture, 100 nM α-MSH was added and cells were treated with one of the test compounds for an additional 72 hrs at 37° C. The cells were then washed with ice cold phosphate buffer and lysed with phosphate buffer (pH 6.8) containing 1% Triton-X (500 μL/well). The plates were frozen at −80° C. for 30 min. After thawing, 100 μL of 1% L-DOPA was added to each well. Following incubation at 37° C. for 2 hrs, the absorbance was measured at 490 nm.

EXAMPLE 7

Anti-Alopecia (Hair Cell Growth Promoting) Activity

A. Cell line: Human follicle dermal papilla (HFDP) cells.
B. Cell seeding in 96 well plate: In culture medium D-MEM medium containing 50 mL of papilla cell growth medium (PCGM), 0.5 mL of fetal calf serum (FSC), 0.5 mL of BPE, 0.25 mL of Cyp, and 0.25 mL of ITT in 51.5 mL total volume.
C. Inhibitor Stocks in DMSO (100 μM).
D. Trypan Blue assay for cell viability/growth (4): HFDP cells were collected and diluted in medium containing Dulbecco's modified minimum essential medium (D-MEM) and 10% fetal bovine serum (FBS) at cell density of $1\times10^4$ cell/mL. Then, 200 μL of cell suspension (2,000 cells/well) was transferred into each well of collagen-coated 96 well plate, and cells were incubated for 37° C., under 5% $CO_2$ for 3 days. The medium was removed, and 200 μL of samples prepared in D-MEM only was added. After 4 days incubation, cell were detached from the plate by a protease called accutase, and stained with Trypan blue, and the number of unstained (viable) cells was counted in a hemocytometer.

EXAMPLE 8

Anti-PAK1 Activity in Cell Culture (4)

A. Cell line: Human lung cancer (A549) cells.
B. Cell seeding in 6-well plate with the culture medium (D-MEM).
C. Inhibitor Stocks in DMSO (100 mM).
D. "Macaroni-western" (IP) ATP-Glo kinase assay: The kinase activity of PAK1 in A549 (or B16F100 cells was measured by a method called "Macaroni-Western" (IP) ATP-Glo kinase assay. Briefly, cells (2×105 cells/mL) were pre-cultured on 6-well plate for 24 hrs in the medium. Then cells were treated with a test compound in the same medium for additional 24 hrs. Cells were disrupted by lysis buffer containing 50 mM Tris-HCl pH 7.5 and 150 mM NaCl and 1% Triton-X. For the immunoprecipitation (IP) of PAK1, the cleared cell lysates were incubated with anti-PAK1 IgG (1:50 dilution) and protein A-agarose beads for 1-2 hrs in cold room with continuous shaking by a rotary mixer (Nissin, Suginami-ku, Tokyo, Japan). The resultant IP (PAK1) from each lysate was incubated with ATP-Glo kinase assay kit (Promega) in the presence of ATP and MBP (myelin basic protein) for 1 hr at 37° C., and the remaining ATP level was measured by the ATP-dependent Luciferin-Luciferase reaction which eventually generates a luminescence. The final suspension was centrifuged, and the supernatant was transferred to 96-well plate for reading. Luminescence was recorded by MTP-880Lab microplate reader (Corona, Hitachinaka-ku, Ibaraki, Japan) with an integration time of 0.5 s per well.

EXAMPLE 9

In Vitro Anti-COX-2 (Cyclooxygenase-2) Activity (5)

The effect of Ketorolac and PRC-15K (both in racemic form) on COX-2 was assayed in vitro, essentially according to the procedure previously published (5). Briefly, the recombinant human COX-2 was treated with either Ketorolac or PRC-15K at concentrations ranging 5-200 nM for 2 or 5 min (depending on the chemical nature of the test compounds) at room temperature in the presence of arachidonic acid, to measure the remaining COX-2 activity at 590 nm. The COX-2 activity without these test chemicals was used as the negative control for calculating their anti-COX-2 activity. Since PRC-15K alone shows the significant absorbance at 590 nm, the absorbance at 590 nm of each PRC-15K sample (5-20 nM) without COX-2 were used as the blank for the correction.

EXAMPLE 10

Cell-Permeability (Intracellular Uptake) Assay

For measuring the uptake of both original acids and their esters into cells, a drug-resistant breast cancer cell line (EMT6) was chosen, as it survives the treatment with either acids or their esters at 100 uM for 24 hrs. The uptake of each compound (100 uM) into $1\times10^5$ cells mainly during the first 1 hr was quantitated by separation of either original acids or their esters taken by cells through HPLC column chromatography, and the amount of each compound was estimated by photometry at the wavelength 322 nm.

EXAMPLE 11

Anti-Cancer Activity of Triazolyl Esters Compared to Original Acids

Artepillin C Ester

The IC50 against the growth of A549 human lung cancer cells=250 nM (100 fold more potent than ARC). The IC50 against the PAK1-dependent melanogenesis of melanoma (B16F10) cells=250 nM. The ED for the growth of human hair (HFDP) cells=20 nM (1000 fold more potent than ARC). The anti-PAK1 activity in cell culture is around 45% inhibition at 1 mM. Cell-permeability is at least 8 fold more cell-permeable than ARC through EMT6 breast cancer cells. Comparative improvement in IC50 is shown in Table 1.
Caffeic Acid Ester
The IC50 against the growth of A549 human lung cancer cells=225 nM (over 400 fold more potent than CA). The IC50 against the PAK1-dependent melanogenesis of melanoma (B16F10) cells=225 nM. The anti-PAK1 activity in cell culture is around 35% inhibition at 1 μM. Cell-permeability: at least 20 fold (probably up to 70 fold) more cell-permeable than CA through EMT6 breast cancer cells. Comparative improvement in IC50 is shown in Table 1.
Ketorolac Ester
The IC50 against the growth of A549 human lung cancer cells=24 nM (over 500 fold more potent than Ketorolac). The IC50 against the PAK1-independent growth of melanoma (B16F10) cells=5 nM (over 6000 fold more potent than Ketorolac). The anti-PAK1 activity in cell culture: around 50% inhibition at 70 nM (over 30 fold more potent than Ketorolac). Anti-COX-2 activity in vitro: IC50 against human COX-2=6 nM (over 20 fold more potent than Ketorolac). Cell-permeability: at least 10 fold more cell-permeable than Ketorolac through EMT6 breast cancer cells. The comparative improvement in IC50 is shown in Table 1.

TABLE I

Potentiation of Anti-cancer Activity by Esterization of Acidic PAK1-blockers

| Triazolyl esters | IC$_{50}$ of Esters | IC$_{50}$ of Original Acids |
|---|---|---|
| Artepillin C (100 fold) | 250 nM (PRC-15A) | 25,000 nM (ARC) |
| Caffeic acic (>400 fold) | 225 nM (PRC-15C) | 100,000 nM (CA) |
| Ketorolac (>500 fold) | 24 nM (PRC-15K) | 13,000 nM (Ketorolac) |

IC$_{50}$: Concentrations for 50% inhibition against the growth of A459 lung cancer cell line It is apparent from the above that the arrangements described are applicable to compositions and treatments for PAK1-dependent diseases/disorders. It can be used in the medical industry for cancer treatment area or for other treatments to suppress PAK1. It can be used in the medical or cosmetic industry for treating cancer (mainly solid tumors), and a variety of other diseases such as AIDS, malaria, viral/bacterial infections such as influenza, Alzheimer's Disease, Huntington's, diabetes (type 2), neurofibromatosis, Parkinson's disease, tuberous sclerosis, inflammatory diseases such as asthma and arthritis, hypertension, epilepsy, depression, learning disability, schizophrenia and autism associated with fragile X syndrome (FXS), as well as alopecia (hair loss), hyper-pigmentation and osteoporosis. Therefore the invention is applicable to a wide range of therapeutic medical or cosmetic industries.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Although the invention has been described with reference to specific examples, it will be appreciated by those skilled in the art that the invention may be embodied in many other forms. Steps may be added or deleted to methods described within the scope of the present invention.

The following references are cited herein.

1. Maruta, H. *Phytother Res* 28:656-72 (2014).
2. Hirokawa et al. Cancer Lett. 245:242-51 (2007).
3. Guo et al. Mol Cancer Ther. 14:2215-27 (2015).
4. Nguyen et al. Drug Discov Ther. 9:289-295 (2015).
5. Nguyen et al. Molecules, 20:14334-14347 (2015).

What is claimed is:

1. A compound of Formula I:

wherein,
$R_1$ is a decarboxylated acidic PAK1 blocker; and
$R_2$ is an aromatic group; or
a pharmaceutically acceptable salt thereof.

2. The compound of claim 1, wherein R1 is a decarboxylated form of artepillin C, caffeic acid, R-ketorolac, captopril, CDDOITP151, Mimosinyl-Phe-Phe, Crocetin monoester, CX-4945, rosmarinic acid, or nicotinic acid (Niacin).

3. The compound of claim 1, wherein R2 is ortho-phenol, ortho-methoxy benzene, ortho-aniline, ortho-arginine phenyl ester, or ortho-am inohexyl benzene.

4. A pharmaceutical composition, comprising the compound of claim 1 and a pharmaceutically acceptable carrier.

5. The pharmaceutical composition of claim 4, wherein a concentration of the compound in the composition is from about 5 nM to about 250 nM.

6. A method for treating a PAK1 dependent disease or disorder in a subject in need thereof, comprising a step of: administering to the subject a therapeutically effective amount of the compound of claim 1 or the pharmaceutically acceptable salt thereof.

7. The method of claim 6, wherein the compound has a cell permeability about 100 fold to about 500 fold of an acidic PAK1 blocker.

8. The method of claim 6, wherein the PAK1 dependent disease or disorder is cancer, Alzheimer's disease, Parkinson's disease, Huntington's disease, arthritis, asthma, multiple sclerosis, stomach ulcer, malaria, AIDS, diabetes (type 2), hypertension, epilepsy, schizophrenia, autism, depression, obesity, hyper-pigmentation, alopecia, pain and osteoporosis or a combination thereof.

9. The method of claim 8, wherein said cancer is pancreatic cancer, colon cancer, breast cancer, prostate cancer, lung cancer, brain cancer (glioma), neurofibromatosis type I or neurofibromatosis type II, tuberous sclerosis complex, multiple myeloma or a combination thereof.

10. A method for treating a cancer in a subject having an increased resistance to a conventional anti-cancer therapy, comprising a step of: administering to the subject a therapeutically effective amount of the compound of claim 1.

11. The compound of claim 1, wherein R1 is a decarboylated form of artepillin C, caffeic acid or R-ketorolac.

12. The compound of claim 1, wherein R2 is ortho-methoxy benzene or ortho-chloro benzene.

13. A cosmetic composition comprising the compound of claim 1 or the pharmaceutically acceptable salt thereof and a cosmetically acceptable adjuvant, carrier or diluent.

14. A method for improving skin-whitening in a subject in need thereof, comprising administering the cosmetic composition of claim 13 to the subject.

15. A method for promoting hair growth in a subject in need thereof, comprising: administering the cosmetic composition of claim 13 to the subject.

* * * * *